United States Patent [19]

Imran

[11] Patent Number: 5,403,297
[45] Date of Patent: Apr. 4, 1995

[54] ELONGATE DEVICE HAVING STEERABLE DISTAL EXTREMITY AND PROXIMAL BEND AND METHOD

[75] Inventor: Mir A. Imran, Palo Alto, Calif.

[73] Assignee: Intelliwire, Inc., Sunnyvale, Calif.

[21] Appl. No.: 116,401

[22] Filed: Sep. 3, 1993

[51] Int. Cl.⁶ .......................................... A61M 37/00
[52] U.S. Cl. .................................... 604/281; 128/657
[58] Field of Search ................. 128/657, 772; 604/95, 604/280–283

[56] References Cited

U.S. PATENT DOCUMENTS

| | | | |
|---|---|---|---|
| 4,543,090 | 9/1985 | McCoy | 604/95 |
| 5,143,085 | 9/1992 | Wilson | 128/657 |
| 5,152,748 | 10/1992 | Chastagner | 604/281 |

FOREIGN PATENT DOCUMENTS 5130970  5/1993  Japan .................... 604/281

Primary Examiner—Max Hindenburg
Attorney, Agent, or Firm—Flehr, Hohbach, Test Albritton & Herbert

[57] ABSTRACT

Elongate device for insertion into a body cavity comprising an elongate tubular member having proximal and distal extremities. First and second elongate temperature-activated shape-memory elements are carried by and are disposed within at least a portion of the elongate tubular member. The first and second shape-memory elements are substantially circular in cross-section along substantially their entire length. The shape-memory elements have end portions carrying indicia permitting the shape-memory elements to be oriented circumferentially in the elongate tubular member. Heat is supplied to the shape-memory elements to cause bending to occur in the shape-memory elements to form a bend in that portion of the elongate tubular member in which the shape-memory elements are disposed.

14 Claims, 1 Drawing Sheet

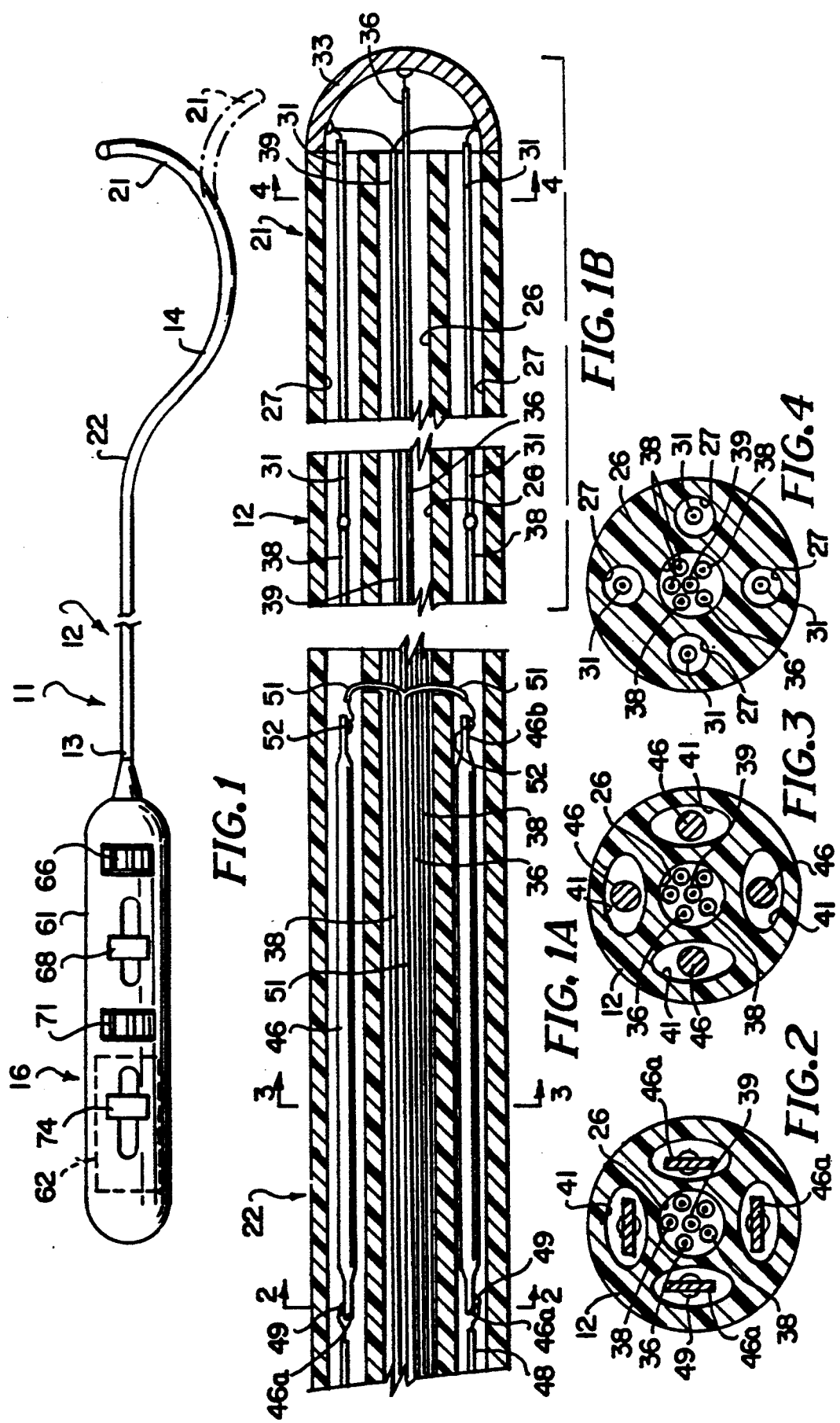

ELONGATE DEVICE HAVING STEERABLE DISTAL EXTREMITY AND PROXIMAL BEND AND METHOD

This invention relates to an elongate device having steerable distal extremity and proximal bend and method and more particularly to a guide wire catheter having a steerable distal extremity and a proximal bend.

In U.S. Pat. No. 4,543,090, issued on Sep. 24, 1985 to McCoy there is disclosed a steerable and aimable catheter which utilizes a plurality of temperature-activated memory elements which are incorporated into the distal extremity of a tubular member. Therein, it is disclosed that the memory elements may be wires or flat strips which are formed of a mechanical memory metal such as a nickel-titanium alloy. Each temperature-activated memory element is originally annealed into its first preset shape. The memory elements are then cooled and straightened to their second shape before incorporation into the distal extremity of the tubular member. The memory elements are again heated to a predetermined transitional temperature to urge them to return to their first or preset shape. McCoy also teaches that by applying an opposing force to an element 20 that has assumed its preset shape it can be moved to a second shape. McCoy teaches that the transitional temperature can be any temperature above body temperature, as for example from 100° to 150° F. It is also pointed out that each memory element must be coupled to at least one other memory element so that when one of the memory elements is heated, it applies a force to the other memory element. As shown in FIG. 4 of McCoy, four temperature-activated memory elements in the form of flat strips are provided which are arranged in two diametrically opposed pairs offset by 90° with respect to each other. McCoy states that with such an arrangement, the distal end 16 may be deflecting in at least four different directions by applying electrical current or voltage to one of the memory elements 20. It is believed that this teaching of McCoy is erroneous because with these four flat rectangular cross-section strips 20, any attempt to bend one pair of strips in one direction would be prevented by the other pair of two strips disposed at 90° with respect thereto. These four stripes 20 are equivalents to four splints used on a broken leg to prevent bending of the leg. Thus the arrangement shown in FIG. 4 and also in FIG. 6 of McCoy discloses inoperative embodiments to attain four way bending. Even when only two of the elements are provided in a single pair, the arrangement disclosed by McCoy is still undesirable because bending would only be permitted in two directions in a single plane. The distal extremity of such a catheter would be very stiff in every other direction other than in the plane of bending. There is therefore a need for a new and improved device in the form of a catheter and/or a guide wire which overcomes the above-named disadvantages.

In general, it is an object of the present invention to provide a elongate device having steerable distal extremity and proximal bend and method which bending can occur in any one of a number of directions.

Another object of the invention is to provide a device of the above character which is relatively flexible.

Another object of the invention is to provide a device and method of the above character in which shape-memory elements are utilized.

Another object of the invention is to provide a device and method of the above character in which the shape-memory elements only need to be approximately as long as the circumference of the bend.

Another object of the invention is to provide a device and method of the above character in which the device can be provided with a distal curve and a proximal curve.

Another object of the invention is to provide a device and method of the above character in which the distal and proximal curves can be in relatively close proximity to each other.

Another object of the invention is to provide a device and method of the above character in which the shape-memory elements are generally circular in cross section.

Another object of the invention is to provide a device and method of the above character in which the shape-memory elements can be oriented circumferentially within the device.

Another object of the invention is to provide a device and method of the above character in which pull wires are utilized for forming the distal curve.

Additional objects and features of the invention will appear from the following description in which the preferred embodiments are set forth in detail in conjunction with the accompanying drawings.

FIG. 1 is a side elevational view of an elongate device having a steerable distal extremity and having a proximal bend.

FIG. 1A is a partial cross-sectional view of the portion of the device shown in FIG. 1 having the proximal bend therein.

FIG. 1B is an enlarged cross-sectional view of a portion of the device shown in FIG. 1 having a distal bend.

FIG. 2 is a cross-sectional view taken along the line 2—2 of FIG. 1A.

FIG. 3 is a cross-sectional view taken along the line 3—3 of FIG. 1A.

FIG. 4 is a cross-sectional view taken along the line 4—4 of FIG. 1B.

In general, the elongate device of the present invention is for use for insertion into a body cavity. It is comprised of an elongate tubular member having proximal and distal extremities. The first and second elongate temperature-activated shape-memory elements are carried by and are disposed within at least a portion of the elongate tubular member. The first and second shape-memory elements are substantially circular in cross section and have end portions which can be used for identifying the orientation of the shape-memory elements. Means is provided for supplying heat to the shape-memory elements that cause bending to occur in the shape-memory elements. The shape-memory elements have sufficient mass so as to be capable to cause bending of the portion of the elongate flexible tubular member in which the shape-memory elements are disposed.

More in particular, the elongate device 11 as shown in FIG. 1 is designed for insertion into a body cavity. It is provided with an elongate tubular member 12 which is provided with proximal and distal extremities 13 and 14. The proximal extremity 13 is secured to a handle 16 of the type which has been sized to fit into a human hand for a purpose hereinafter described. The distal extremity 14 is provided with a distal bend 21 and a proximal bend 22. The enlarged cross-sectional views of the bends 21 and 22 are shown in FIGS. 1B and 1A, respectively.

The elongate tubular member 12 can be formed of a suitable material such as plastic. However, it should be appreciated that other materials such as stainless steel tubing typically called hypotube can be utilized. If the device 11 is to be a guide wire, the elongate tubular member 12 can have a suitable outside dimension ranging from 0.008" to large as desired, as for example 0.032". It can have a suitable length such as 120–180 centimeters. Thus as shown in FIG. 1B, the distal extremity 21 of the elongate tubular member 12 can be formed of plastic and is provided with a relatively large central lumen 26 extending therethrough with circumferentially spaced-apart lumens 27 spaced around the central lumen 26. The lumens 26 and 27 can have a suitable size, as for example 0.003 inches to 0.010 inches. The central lumen 26 can have a diameter ranging from 0.010" to 0.050" or larger.

Pull wires or pull elements 31 are disposed in the lumens and can be of the type described in co-pending application, Ser. No. 07/793,858, filed on Nov. 18, 1991. As disclosed therein, they can be formed of a material having a negative coefficient of expansion so that when they are heated they will contract. A hemispherical tip 33 formed of a suitable conducting material such as platinum is secured to the distal extremity 14 of the elongate tubular member 12 by suitable means such as an adhesive. The pull wires 31 are secured to the tip 33 by a suitable means such as welding and serve as safety wires for ensuring that the tip 33 remains with and does not separate from the distal extremity of the elongate tubular member 12.

It should be appreciated that in the event as desired to fabricate the elongate tubular member 12 from a conducting metal, as for example stainless steel the pull wires 31 can themselves be insulated so they are insulated from the elongate tubular member 12.

As shown four of such pull wires 31 are provided and are secured circumferentially around the inner perimeter of the tip 33. If the tip 33 is used as an ablation electrode as shown, a separate conductor 36 is bonded to the tip and extends proximally through the central bore 26. The proximal extremities of the pull wires 31 are secured to conductors 38 which extend proximally through the central bore 26 through the proximal extremity 13 of the elongate tubular member 12. A return conductor 39 is bonded to the distal extremities of the pull wires 31 and extends proximally through the central bore 26 to the proximal extremity 13.

In the proximal bend portion 22, the elongate tubular member 12 is provided with moon-shaped or crescent-shaped lumens 41 which are spaced circumferentially around the central lumen 26, as for example they can be spaced 90° apart as shown in FIGS. 2 and 3. Shape-memory elements 46 are provided in the lumens 41 and generally have a length which is approximately the same as the circumference of the proximal bend 22. Typically the shape-memory elements can be formed of a nickel-titanium alloy of a type which can be temperature actuated. As can be seen from FIG. 3, the shape-memory elements 46 are substantially circular in cross section and have flattened end portions 46a and 46b which serve as indices carried by the end portions permitting the shape memory element to be oriented in the elongate tubular member 12. Typically the flattened end portions 46a and 46b are provided before the shape-memory element has been programmed with a desired shape memory. This makes it possible to provide a shape memory program which corresponds to the orientation of the end portions 46a and 46b. The device 11 shown in FIG. 1 can have the end portions 46a and 46b oriented to provide the desired bend in the proximal bend 22. The proximal or flattened end portions 46a are connected to conductors 48 by a suitable means such as solder connections 49. The conductors 48 extend through the lumens 41 to the proximal extremity 13 of the elongate tubular member 12. The flattened distal end portions 46b are also connected to conductors 51 by solder joints 52. As shown, the conductors 51 can be interconnected to provide a common ground return conductor 51 for the shape-memory elements 46. The ground return 51 extends to the proximal extremity through the central lumen 26.

Thus, it can be seen that the shape-memory elements 46 are substantially circular in cross section substantially throughout their entire length except for the flattened end portions 46a and 46b thus making it possible for the shape-memory elements 46 to bend in any direction and not be limited to bending in only two directions in one plane if they were formed of flat strips extending their entire length. The shape-memory elements 46 also are formed of a size so that they have a sufficient mass so that they can cause bending of the portion of the elongate tubular member 12 in which the shape-memory elements 46 are disposed. The shape-memory elements 46 typically must have a much greater mass than the pull wires 31 because the pull wires 31 operate on the principle of contraction when the material having a negative coefficient of expansion is heated to cause pulling forces to be applied to the tip 33 to cause bending of the portion of the flexible elongate tubular member 12 in which they are disposed. By way of example, assuming that the device 11 is in the form of a guide wire, the flexible elongate member 12 can have an outside diameter of 0.10" the pull wires 31 could have a suitable diameter such as 0.001" and the shape-memory elements 46 could have a diameter such as 0.003" to provide a cross-sectional mass ratio of approximately six for the shape-memory element 46 with respect to one for the cross-sectional mass of the pull wires 31 because the cross-sectional mass is a function of the radius squared.

All the conductors 36, 38 and 39 as well as the conductors 48 and 51 extend to the proximal extremity 13 of the elongate tubular member 12 and extend into the handle 16. The handle 16 consists of a housing 61 which can be cylindrical in cross section and elongate and sized to fit in a human hand, as for example having a diameter of one and one-half to two inches and a length of five to six inches. The housing 61 contains a battery power supply 62 for supplying electrical energy to the pull wires 31 and to the shape-memory elements 46 through suitable controls. As for example, there is provided a rotary potentiometer (not shown) which has a control knob 66 rotatably mounted in the housing 66 and a linear potentiometer (not shown) which is provided with a slider actuator or knob 68 which is utilized for controlling the operation of the pull wires 31 for controlling the distal bend 21. There is also provided in the housing 61 a rotary potentiometer (not shown) which has a control knob 71 and a linear potentiometer (not shown) which is provided with a slider control member or a knob 74 which is utilized for supplying energy for heating the shape-memory elements 46 for causing heating of the shape-memory elements 46 to control the proximal bend 22. A more detailed disclosure of the type of controls which can be provided in the housing 61 are described in U.S. Pat. No. 5,238,005 and in application, Ser. No. 07/983,999, filed Dec. 1, 1992 and application, Ser. No. 07/983,837, filed Dec. 1, 1992.

Operation and use of the device 11 may now be briefly described as follows. Let it be assumed that the device 11 is in the form of a guide wire which is to be utilized in conjunction with an angioplasty procedure. As is typical in such procedures, the guide wire can be introduced through the femoral artery of the patient and advanced towards the heart. The cardiovascular surgeon by watching the radiopaque tip 33 can observe the advancement of the tip into the arterial vessel. The bending of the distal extremity 14 can be controlled by actuation of the slider control member 68 and the rotational position of the tip can be controlled by rotation of the knob 66 to supply heat by heating the same by passing electrical current through the pull wires. It can be seen that the distal bend can be made so that the tip 33 can be rotated through 360° about the axis of the flexible elongate tubular member 12 and similar bends of various conformations can be achieved, as for example extending through 180° as shown in dotted lines in FIG. 1. With respect to actuation of the pull wires 31, the response time is substantially instantaneous because of the low mass of the pull wires 31. This is advantageous because the surgeon can in effect operate in real time in navigating a tortuous vessel of the heart.

The shape and direction of the bend 22 can be controlled by the control knob 71 and the slider control member 74 by heating the same as by passing electrical current through the shape memory elements. Because of the larger mass of the shape-memory elements 46, the response time is somewhat greater than that for the pull wires 31. This can be readily accommodated by the cardiovascular surgeon because the shape-memory elements 46 are disposed in the proximal bend 22 in which bending can occur more slowly without a big disadvantage. This is true because when a bend is placed in the portion of the elongate tubular member having the proximal bend 22 therein, it is generally unnecessary to make significant changes in the bend once the distal extremity of the guide wire has been advanced into close proximity to the desired location. Most of the steering of the distal extremity of the guide wire is accomplished by the distal bend 21 which does have a fast response time. Thus it can be seen that the combination of the fast response time distal bend 21 with the slower response time proximal bend 22 provides a good combination making it possible to navigate small tortuous vessels in the heart. Combining the two types of bends is also advantageous in that it is possible to place a shape-memory element type of bend such as a proximal bend 22 in close proximity to the distal bend 21 utilizing the pull wires. This is true, because typically, the shape-memory elements to accomplish the desired amount of bending require a lesser length of the elongate tubular member 12 than do the pull wires 31 in the distal bend 21 because with the pull wires, the degree of bending is determined by the amount of contraction of the pull wires upon heating which is determined by the length of the pull wires. Thus, to achieve a certain amount of bending in the elongate tubular member 12 requires a greater length when utilizing pull wires 31 than when utilizing shape-memory elements 46. Thus it can be seen that the pull wire elements 31 have very desirable attributes which can be particularly advantageous when combined with the shape-memory elements 46 to provide a combination of features which often is very desirable for guide wires, catheters and the like.

Although the shape-memory elements 46 have been provided in a proximal bend 22 it should be appreciated that shape-memory elements having the circular cross section along substantially the entire length can be utilized in other portions of the flexible elongate member as long as a substantially instantaneous response time is not required. Similarly it should be appreciated that the pull wires also can be utilized in different locations other than for the distal bend 21 where a fast response time is desired for the bend with the only disadvantage being that the pull wires typically will take a greater length in the flexible elongate element 12 than would the shape-memory elements 46. Also it should be appreciated that both the proximal bend 22 and the distal bend 21 can be formed of pull wires 31 or solely of shape-memory elements 46 with the sacrifice being with respect to utilization of two sets or more of the pull wires requiring a greater length of the elongate tubular member 12 for accommodating the bends because of the spacing required between the bends. In such an arrangement, fast response times can be obtained for both of the proximal and distal bends. Conversely, if only shape-memory elements 46 are utilized for both the distal and proximal ends 21 and 22, they can be placed closer together along the length of the elongate tubular member providing more compact bends but the increased response times.

Thus, it can be seen that the desired characteristics for the device 11 can be selected in accordance with the type of bend desired and the response time required for making the bends. The various features of the present invention make it possible to provide devices having different characteristics to meet different applications.

From the foregoing it can be that there has been provided an elongate device which has a distal extremity which can be bent in any direction with a desired curvature to negotiate tortuous vessels.

What is claimed is:

1. In an elongate device for insertion into a body cavity, an elongate tubular member having proximal and distal extremities, first and second elongate temperature-activated shape-memory elements carried by and disposed within at least a portion of the elongate tubular member, said first and second shape-memory elements being substantially circular in cross-section along substantially the entire length, said shape-memory elements having end portions carrying indicia permitting the shape-memory elements to be oriented circumferentially in the elongate tubular member and means for supplying electrical energy to the shape-memory elements to cause bending to occur in the shape-memory elements to form a bend in that portion of the elongate tubular member in which the shape-memory elements are disposed.

2. A device as in claim 1 wherein said means for supplying heat to the shape-memory elements includes means for supplying electrical energy to the shape-memory elements.

3. A device as in claim 1 wherein said end portions carrying indicia are end portions which are rectangular in cross section.

4. A device as in claim 1 wherein said shape-memory elements have sufficient mass to cause bending of said portion of the elongate tubular member when the shape-memory elements are heated.

5. In an elongate device for insertion into a body cavity, an elongate tubular member having proximal and distal extremities, first and second elongate temperature-activated shape-memory elements carried by and disposed within at least a portion of the elongate tubular member, said first and second shape-memory elements being substantially circular in cross-section along substantially the entire length, said shape-memory elements having end portions carrying indicia permitting the shape-memory elements to be oriented circumferentially in the elongate tubular member, means for supplying heat to the shape-memory elements to cause bending to occur in the shape-memory elements to form a bend in that portion of the elongate tubular member in which the shape-memory elements are disposed and pull wire means formed of a material having a negative coefficient of expansion disposed in the distal extremity of the elongate tubular member for forming the distal bend.

6. A device as in claim 5 wherein said shape-memory elements are disposed in the elongate tubular member in close proximity to the pull wire means to form a proximal bend in the distal extremity of the elongate tubular member.

7. A device as in claim 6 wherein said pull wires elements have a mass which is substantially less than the mass of the shape-memory elements so that a fast response time is provided by the pull wire means in comparison to the response time of the shape-memory elements when the pull wires and/or the shape-memory elements are heated.

8. In an elongate device, a flexible elongate tubular member having proximal and distal extremities, pull wire means for forming a distal bend in the distal extremity and shape-memory element means for forming a proximal bend in the distal extremity of the flexible elongate tubular member, said pull wire means being formed of pull wire elements formed of a material having a negative coefficient of expansion which contracts upon being heated and wherein said shape-memory elements bend upon being heated and means for selectively supplying heat to the pull wire elements and the shape-memory elements to cause a distal bend and a proximal bend to be formed in the distal extremity of the flexible elongate member.

9. A device as in claim 8 wherein said pull wire elements have a mass which is substantially less than the mass of the shape-memory elements so that the response time provided by the pull wire elements is substantially faster than that provided by the shape-memory elements.

10. A device as in claim 8 wherein said shape-memory elements comprised of at least first and second shape-memory elements which are substantially circular in cross section substantially along their entire length.

11. A device as in claim 8 wherein said proximal bend is disposed in relatively close proximity to the distal bend in the distal extremity of the flexible elongate tubular member.

12. A device as in claim 9 wherein said pull wire means includes at least three pull wire elements.

13. In a method for controlling the distal extremity of a flexible elongate tubular member, forming distal and proximal bends in the distal extremity of the flexible elongate member, causing a change in the distal bend which is at a rate substantially greater than the rate at which a change in the proximal bend can be achieved.

14. A method as in claim 13 together with the step of forming the proximal bend in a location which is immediately adjacent the distal bend.

* * * * *